United States Patent [19]

Hymanson

[11] Patent Number: 4,767,412
[45] Date of Patent: Aug. 30, 1988

[54] FINGER GUARDS

[75] Inventor: Victor Hymanson, Whitefield, United Kingdom

[73] Assignee: Seldoren Limited, Bury, United Kingdom

[21] Appl. No.: 10,331

[22] Filed: Feb. 3, 1987

[30] Foreign Application Priority Data

Jun. 10, 1986 [GB] United Kingdom ................ 8614029
Jul. 2, 1986 [GB] United Kingdom ................ 8616190
Jan. 13, 1987 [GB] United Kingdom ................ 8700707

[51] Int. Cl.$^4$ .............................................. A61M 5/32
[52] U.S. Cl. .................................... 604/192; 604/263
[58] Field of Search ................ 604/192, 193, 187, 263

[56] References Cited

U.S. PATENT DOCUMENTS 4,317,446 3/1982 Ambrosio et al. .................. 604/193
4,485,918 12/1984 Mayer .............................. 604/263 X

FOREIGN PATENT DOCUMENTS 3433359 4/1986 Fed. Rep. of Germany ...... 604/192
2586568 3/1987 France ............................... 604/263

Primary Examiner—John D. Yasko
Attorney, Agent, or Firm—Pearson & Pearson

[57] ABSTRACT

A finger guard is provided for use with a storage tube for a hypodermic needle to prevent accidental injury to the person using the needle during replacement thereof in the storage tube. The finger guard comprises a tubular finger gripping portion having a bore therein in which the storage tube is received. Radially inwardly extending deformable flaps grip the storage tube, whereby differing sizes of storage tube may be accommodated. An annular guard portion extends radially outwardly of the finger grip portion at the forward end of the guard to prevent the needle from contact with the fingers when attempting to insert the needle into the storage tube.

8 Claims, 3 Drawing Sheets

FINGER GUARDS

This invention relates to a finger guard for use with a storage tube for a hypodermic needle.

Disposable needles for hypodermic syringes are commonly supplied in sealed storage tubes. When required for use to inject a patient the needle is removed from the tube and after use the needle is inserted back into the tube for disposal. Having regard to the relatively small size of the tube it is not uncommon for a person accidentally to prick a finger whilst trying to insert the used needle back into the tube, and there is the danger that this may transmit infection from the injected patient to the person disposing of the used needle.

An object of the present invention is to provide a guard to protect against such accidental pricking of a person's finger, and preferably a finger guard which is suitable for use with a range of sizes of storage tubes.

The invention provides a finger guard for use with a storage tube for an hypodermic needle, said guard comprising a body having a bore therein and adapted to fit securely yet removably around said storage tube when the latter is received in said bore, said body having a finger grip portion and a guard portion disposed in front of and projecting transversely beyond said finger grip portion.

With this arrangement, with the finger guard body fitted around the tube, the tube can be held in a person's hand with the person's fingers gripping the finger grip portion behind the guard portion. In this position, when inserting a used needle into the tube, if the needle misses the tube it can strike the guard portion rather than the person's fingers.

The bore may be a through bore.

The finger grip portion may be a tubular structure and the guard portion may be an annular structure.

The finger guard may be formed in one piece e.g. as a moulding of a plastics material.

Said guard may comprise a tube gripping portion comprising flap means extending radially inwardly of said body and deformable axially thereof by a storage tube when received in said bore whereby said flap means resiliently grips said storage tube.

Said flap means may be disposed rearwardly of said body and may comprise a plurality of flaps disposed circumferentially of said body.

The invention will now be described further by way of example only and with reference to the accompanying drawings in which.

Figure 1:
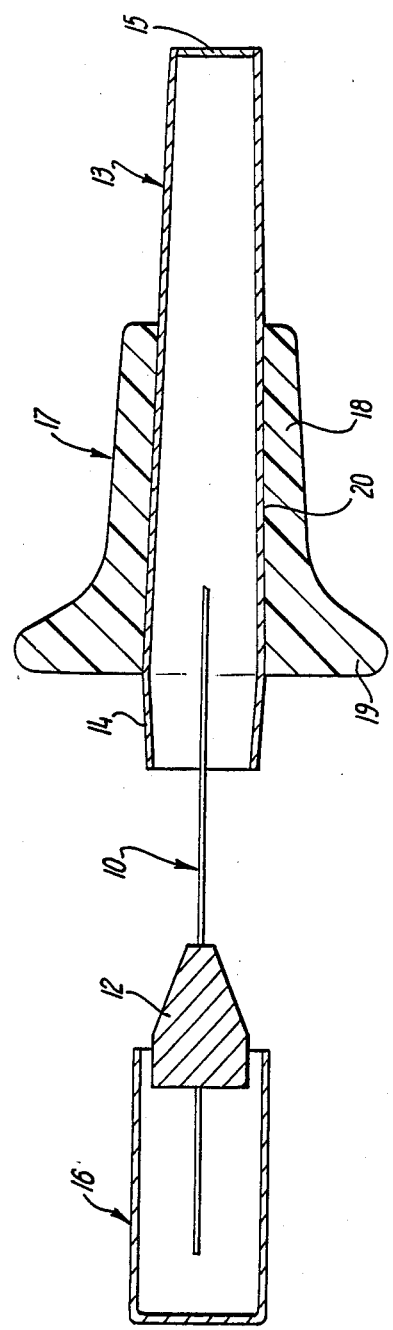
FIG. 1 is a diagrammatic sectional view showing one form of a finger guard according to the invention fitted to a hypodermic needle storage tube.

As shown in FIG. 1, a hypodermic needle 10, for example a disposable needle to be used in dentistry, has an integral mounting member 12. The needle 10 is supplied in a storage tube 13 which has an open end 14 and a closed end 15. The mounting member 12 fits tightly in the open end 14 and the tube 13 is sealed with an end cap 16 which fits over the open end 14.

In use, the cap 16 is detached, and the needle 10 is removed and attached to a syringe (not shown). After use, the needle 10 is detached from the syringe and inserted into the tube 13; the tube 13 is then closed with the cap 16 and disposed of.

As the used needle 10 is inserted into the tube 13, the tube 13 is held with the assistance of a finger guard 17. This comprises a one-piece plastics moulding having an elongate finger grip portion 18 and at one end a circular head portion 19 which projects transversely beyond the finger grip portion 18. A central passage 20 extends through the head and finger grip portions 18,19.

The passage 20 is shaped to correspond with the profile and cross-sectional dimensions of the tube 13 adjacent the closed end 15 so that the guard 17 can easily slide onto the tube 13 at such end. The tube 13 tapers slightly so that the cross-sectional dimensions increase towards the open end 14 whereby the guard 17 wedges and is held securely in position close to the open end 14.

The guard 17 and hence the tube 13 can be held in a person's hand by gripping the finger grip portion 18 whereby the person's fingers are protected against accidental pricking with the used needle by the head portion 19. When the used needle 10 has been safely inserted into the tube 13 the guard 17 can be removed and re-used.

Figure 2:
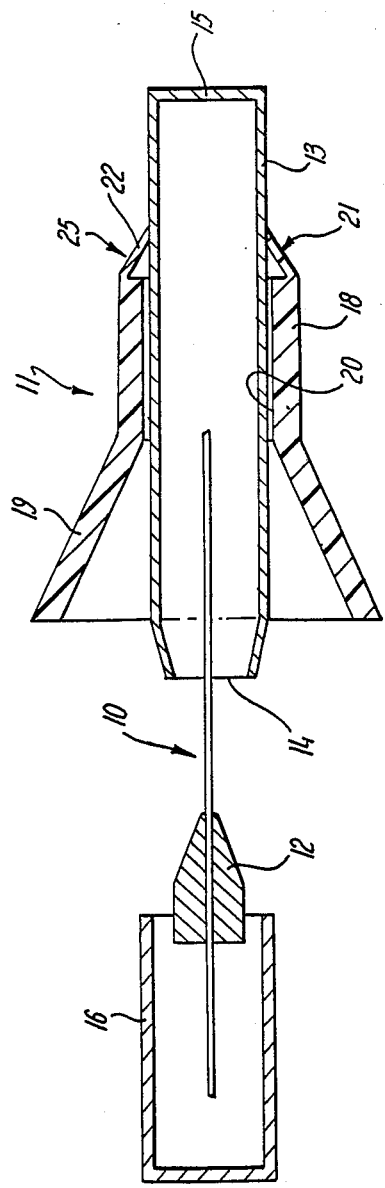
FIG. 2 is a longitudinal sectional view of a second embodiment of finger guard fitted to a storage tube.
Figure 4:
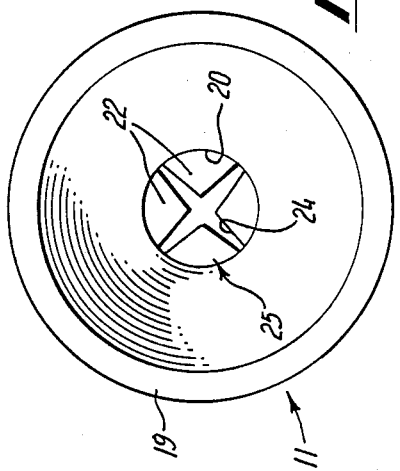
FIGS. 3 and 4 are opposed end views of the guard of FIG. 2.
Figure 3:
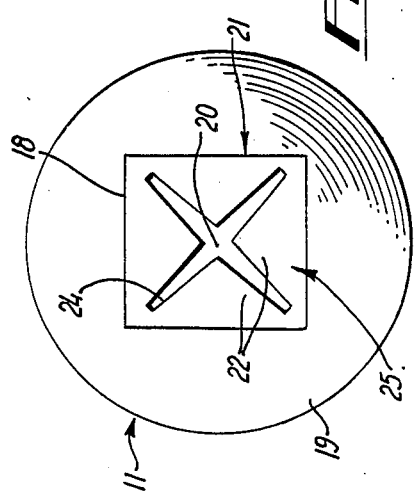

Referring now to FIGS. 2 to 4 there is shown a hypodermic needle 10 with an integral mounting member 12, together with a storage tube 13 and cap 16 as in the previously described embodiment.

To assist in the replacing of the needle 10 in the tube 13 a finger guard 11, which is generally similar to the guard 17 previously described, is used. The guard 11 comprises a one-piece plastics moulding having an elongate, tubular finger grip portion 18. At one, forward, end of the finger grip portion 18 is flared annular guard portion 19 which projects transversely outwardly of the finger grip portion 18. A central bore or passage 20 extends through the guard 11 and finger grip portions 19,18 to receive the storage tube 13 extending therethrough.

In order to accommodate storage tubes 13 of differing diameters within a range of diameters, the guard 11 is provided with a tube gripping portion 21 comprising four flaps 22 which when not in use extend radially inwardly of the body of guard 11. The flaps 22 are deformable axially of the body of guard 11 by the tube 13 and resiliently grip the tube 13 during use.

The guard 11 and hence the tube 13 can be held in a person's hand by gripping the finger portion 18, whereby the person's hand is protected against accidental pricking by the used needle 10 as it is inserted into the open end 14 of the tube 13. When the needle 10 has been safely inserted into the tube 13 the guard 11 can be removed and re-used.

Other embodiments of guard in accordance with the invention will be readily apparent to persons skilled in the art. For example a number other than four flaps may be provided, and the flaps may be disposed at any axial location relative to the finger gripping part 18 instead of being at the rear end thereof remote from the guard portion 19.

Figure 5:
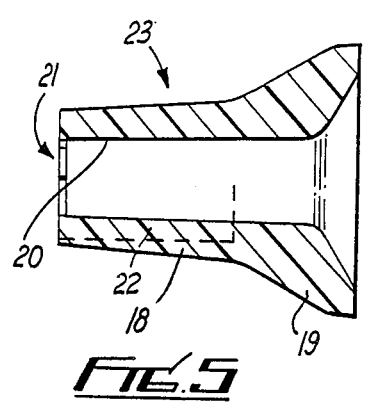
FIGS. 5 to 8 are a longitudinal section and an end view respectively of other embodiments of finger guard.
Figure 6:
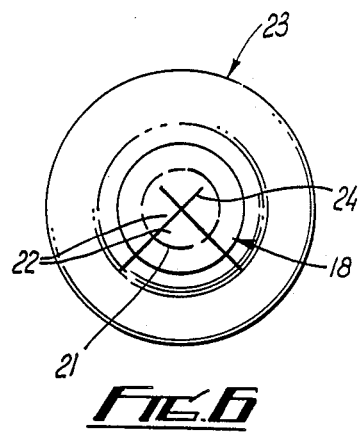

An alternative embodiment of guard 23, which is similar in construction to guard 11 described above, is shown in FIGS. 5 and 6, corresponding parts being identified with the same reference numerals as those used in relation to the guard 11. In both cases the flaps 22 of guards 23 and 11 are formed by providing radially extending slits 24 in an otherwise closed end 25 of the guard 11,23. This embodiment, as shown in the upper halves of FIGS. 5 and 6, may be moulded of any suitable resilient material such as rubber or an elastomeric plastics material. Alternatively this embodiment, as shown in the lower halves of FIGS. 5 and 6, may be moulded of any suitable material, such as papier maché or polypropylene having little resilience. In this case the slits 24 are extended along the finger grip portion 18 as shown so that the guard 23 will deform, in the manner of the embodiment of FIG. 7 described below, to allow insertion and retention of the storage tube 13 in and by the guard 23.

Figure 7:
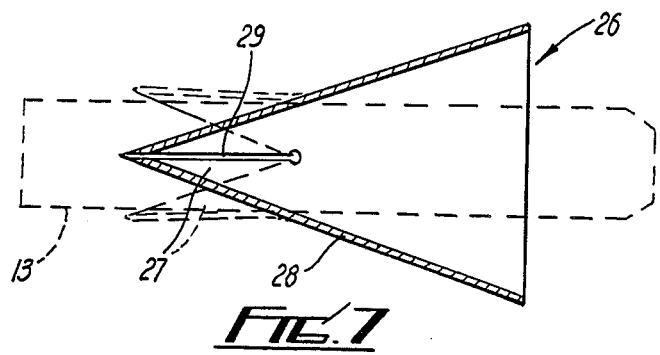
Figure 8:
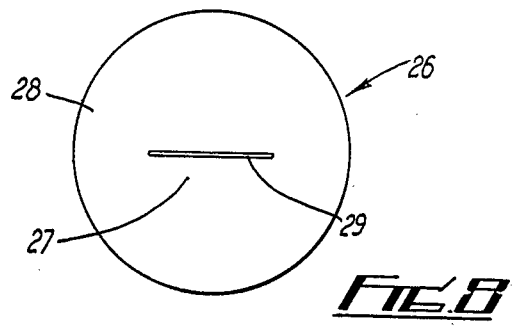

Another alternative embodiment of finger guard 26 is shown in FIGS. 7 and 8. In this case the guard 26 is of a relatively cheap, disposable design, and comprises a coneshaped combined finger grip portion 27 and head portion 28. The guard 26 is made of a stiff paper or paper like plastics material such as polypropylene. The finger grip portion 27 has slits 29 therein extending from the apex of the cone whereby the conical formation of the finger grip portion is deformed by the storage tube 13 on insertion thereof into the ground 26, as shown in broken lines in FIG. 7, such deformation serving to provide a degree of gripping of the tube 13 as well as forming the finger grip portion 27.

We claim:

1. A finger guard for use with a storage tube for a hypodermic needle, said guard comprising a body having a through bore therein and being adapted to fit securely yet removably around said storage tube when the latter is received in said bore, said body having a finger grip portion, a guard portion disposed in front of and projecting transversely beyond said finger grip portion, and a tube gripping portion comprising flap means extending radially inwardly of said body into said through bore and deformable axially thereof by a storage tube when received in said bore, whereby said flap means resiliently grips said storage tube.

2. A finger guard according to claim 1 wherein said finger grip portion is a tubular structure.

3. A finger guard according to claim 2 wherein said guard portion is an annular structure.

4. A finger guard according to claim 1 wherein said flap means is disposed rearwardly of said body.

5. A finger guard according to claim 1 or claim 4 wherein said flap means comprises a plurality of flaps disposed circumferentially of said body.

6. A finger guard according to claim 5 wherein said body has an otherwise closed end and said flaps are formed by a plurality of radially extending slits provided in said otherwise closed end.

7. A finger guard according to claim 1 wherein said finger guard is formed as a single piece.

8. A finger guard according to claim 7 wherein said finger guard is a molding of a plastics material.

* * * * *